United States Patent
Zhou et al.

(10) Patent No.: US 6,277,895 B1
(45) Date of Patent: Aug. 21, 2001

(54) SKELETAL IRON CATALYST HAVING IMPROVED ATTRITION RESISTANCE AND PRODUCT SELECTIVITY IN SLURRY-PHASE SYNTHESIS PROCESSES

(75) Inventors: Peizheng Zhou, Lawrenceville; Lap-Keung Lee, West Windsor, both of NJ (US); Jinglai Zhou, Taiyuan (CN); Yijun Lu, Taiyuan (CN); Guohui Li, Taiyuan (CN)

(73) Assignee: Hydrocarbon Technologies, Inc., Lawrenceville, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/399,852

(22) Filed: Sep. 21, 1999

(51) Int. Cl.$^7$ .............................. C07C 27/00; B01J 25/00; B01J 23/00; B01J 23/40; C22C 38/06
(52) U.S. Cl. .................... 518/715; 518/700; 502/314; 502/327; 502/331; 502/332; 502/336; 502/338; 502/301; 420/77; 420/89; 420/90; 420/91; 420/590
(58) Field of Search ...................... 502/301, 314, 502/327, 331, 332, 336, 338; 420/77, 590, 89, 90, 91; 518/700, 715

(56) References Cited

U.S. PATENT DOCUMENTS 3,862,911 * 1/1975 Chabert ................... 252/470

OTHER PUBLICATIONS

Lupei et al, catalytic activity of skeletal iron catalyst, Tekhnot Inst., Voronezh, USSR, Gos. Univ. No. 4 108–110, 1966.*

* cited by examiner

Primary Examiner—Johann Richter
Assistant Examiner—J. Parsa
(74) Attorney, Agent, or Firm—Fred A. Wilson

(57) ABSTRACT

Particulate skeletal iron catalyst is provided which contain at least about 50 wt. % iron with the remainder being a minor portion of a suitable non-ferrous metal and having characteristics of 0.062–1.0 mm particle size, 20–100 m$^2$/g surface area, and 10–40 nm average pore diameter. Such skeletal iron catalysts are prepared and utilized for producing synthetic hydrocarbon products from CO and H$_2$ feeds by Fischer-Tropsch synthesis process. Iron powder is mixed with non-ferrous powder selected from aluminum, antimony, silicon, tin or zinc powder to provide 20–80 wt. % iron content and melted together to form an iron alloy, then cooled to room temperature and pulverized to provide 0.1–10 mm iron alloy catalyst precursor particles. The iron alloy pulverized particles are treated with NaOH or KOH caustic solution at 30–95° C. temperature to extract and/or leach out most of the non-ferrous metal portion, and then screened and treated by drying and reducing with hydrogen and to provide the smaller size skeletal iron catalyst material. Such skeletal iron catalyst is utilized with CO+H$_2$ feedstream for Fischer-Tropsch reactions in either a fixed bed or slurry bed type reactor at 180–350° C. temperature, 0.5–3.0 mPa pressure and gas hourly space velocity of 0.5–3.0 L/g Fe/hr to produce desired hydrocarbon products.

16 Claims, 1 Drawing Sheet

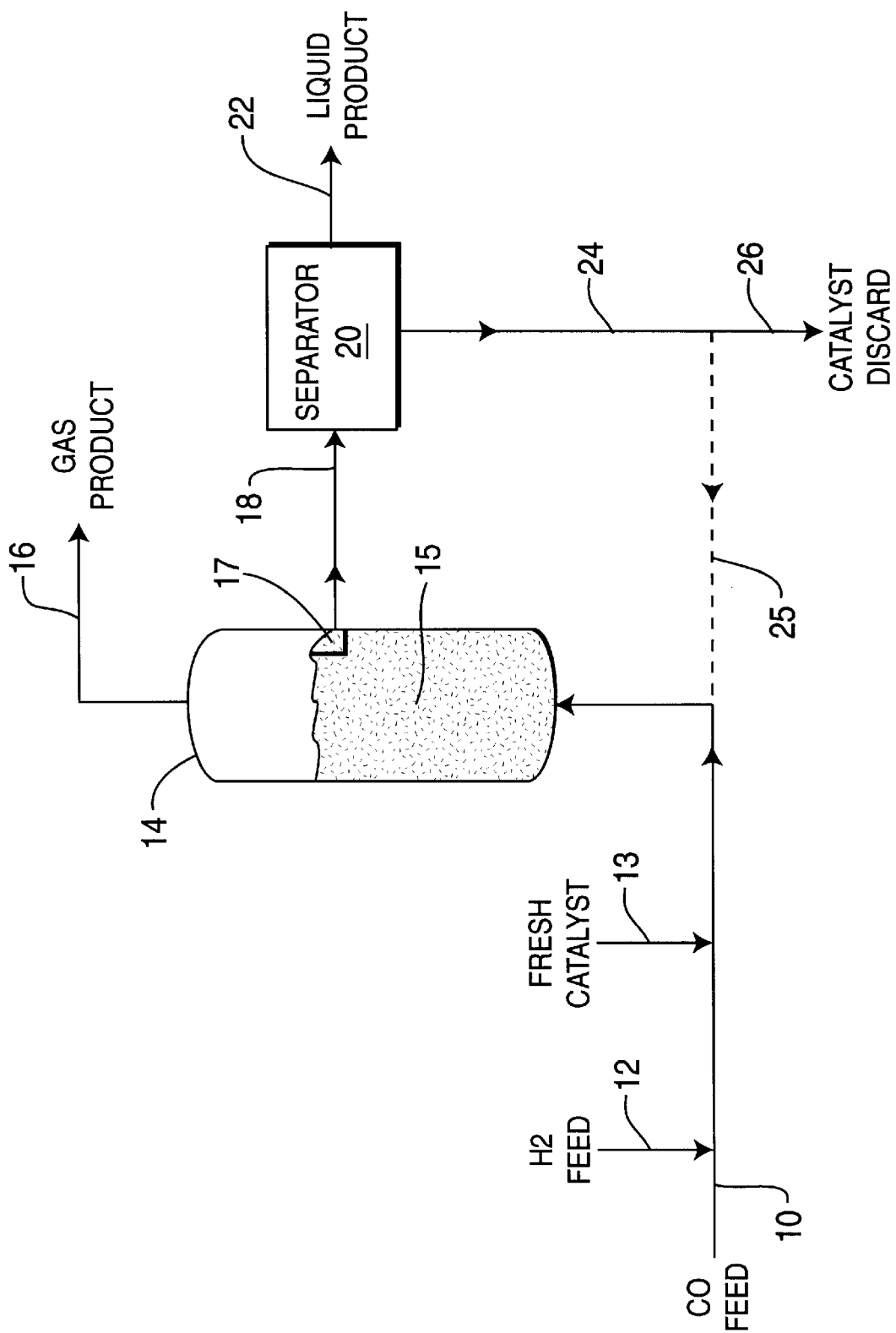

SKELETAL IRON CATALYST HAVING IMPROVED ATTRITION RESISTANCE AND PRODUCT SELECTIVITY IN SLURRY-PHASE SYNTHESIS PROCESSES

BACKGROUND OF INVENTION

This invention pertains to skeletal iron catalyst and its preparation and use in Fischer-Tropsch and similar slurry-phase synthesis processes. More particularly, such skeletal iron catalyst utilized in slurry phase synthesis processes for $H_2+CO$ feedstreams has increased attrition resistance and improved catalyst/product liquid separation, while providing increased selectivity for producing $C_2-C_5$ light olefin products.

Slurry phase Fischer-Tropsch (F-T) synthesis process technology is an important known route for indirect coal liquefaction for synthesis of liquid fuels from $H_2+CO$ feedstreams. Precipitated iron is currently a commonly used catalyst for such Fischer-Tropsch processes. However, precipitated iron catalysts are undesirably fragile and break down easily under reaction conditions into very fine particles, so that separation of such fine catalyst particles from reaction product waxes is difficult to accomplish and results in inferior product quality and significant catalyst loss. Such catalyst problems hinders commercial use of the process. For overcoming this problem, improved skeletal iron catalysts made according to this invention are provided by utilizing caustic extraction and/or leaching non-ferrous metals from specific iron metal alloy particles, and such skeletal iron catalysts have good particle strength and attrition resistance. Literature studies on such catalysts to date have focused on improvement of catalyst activity in simple gas-solid hydrogenation reaction system. Utilization of such improved skeletal iron catalyst in slurry-phase or three-phase gas-liquid-solid Fischer-Tropsch reaction processes fully realizes the advantages of such skeletal iron catalysts. By utilizing such improved skeletal iron catalysts, commercial slurry-bed Fischer-Tropsch synthesis to produce clean hydrocarbon transportation fuels from syngas feedstreams is greatly facilitated.

Light olefins $C_2-$ to $C_5-$ are key component materials in the petrochemical industry as important feedstocks and building blocks for the synthesis of a variety of chemical/petrochemical products. Conventionally, such light olefins are produced by thermal cracking of hydrocarbons ranging from ethane to vacuum gas oils, but not produced directly from natural gas which is essentially methane ($CH_4$). Such thermal cracking is practiced under high temperatures (1,500–1,600° F.), thus requiring costly construction materials and consuming huge amounts of energy for feedstream heating and reaction. A commercially practiced technical route for making light olefins from natural gas is to first convert natural gas via steam reforming into a mixture of hydrogen and carbon monoxide, called synthesis gas or syngas. The current technology of converting syngas into olefins is a two-step catalytic conversion, the first step being catalytic conversion of syngas to methanol, followed by conversion of methanol into olefins. A unique catalyst/technology would be to directly convert synthesis gas into light olefins, without the necessity of an additional step for making methanol as an intermediate material. The skeletal iron catalyst, promoted with other metal ingredients and used in a fixed bed or in slurry-bed reactor system with liquid paraffin as the liquid medium, can advantageously convert syngas directly into light olefins $C_2-C_5-$ under mild conditions in a temperature range of 180–350° C. and a pressure range of 0.5–5.0 mPa.

Thus, this invention provides a unique skeletal iron catalyst having high activity for catalyzing the conversion of syngas feeds to a broad range of hydrocarbon products, and has high selectivity towards light olefins formation in a slurry-phase catalytic reactor system under mild conditions conventionally used in Fischer-Tropsch synthesis, so that the hydrocarbon product is rich in olefins.

SUMMARY OF INVENTION

This invention provides a unique skeletal iron catalyst material advantageously suitable for use in either fixed bed or slurry-phase Fischer-Tropsch synthesis processes for $H_2+CO$ feedstreams for producing clean liquid transportation fuels and light olefin products. The particulate skeletal iron catalyst contains at least 50 wt % iron and preferably 60–90 wt. % iron with remainder being smaller percentages of a non-ferrous metal selected from the group including aluminum, antimony, nickel, tin and zinc and a promotor metal selected from the group of calcium, copper, chromium, magnesium, and potassium. The final skeleton iron catalyst should have a surface area of 10–100 $m^2/g$ and average pore diameter of about 10–40 nm.

The unique skeletal iron catalyst material of this invention is made using a preparation method, which includes providing an iron powder mixed with a suitable non-ferrous metal powder selected from aluminum, antimony, silicon, tin, or zinc sufficient to provide 20–80 w. % iron, together with 0.01–5 wt. % of a promotor metal powder selected from calcium, copper, chromium, magnesium, or potassium. The mixed metal powders are heated and melted together to form an iron alloy precursor material which is then pulverized to 0.1–10 mm (100–10,000 micron) particle size, followed by extracting and/or leaching the major portion of the non-ferrous metal from the iron using a suitable caustic solution of NaOH or KOH, and leaving mainly the iron portion as the skeletal iron catalyst material. The catalyst may be further pulverized and has smaller particle size surface area of 20–100 $m^2/g$ and an average pore diameter of 10–40 run.

The preparation method and pretreatment procedures for this skeletal iron catalyst are relatively simple and inexpensive. This skeletal iron catalyst has good particle strength and attrition resistance, and activity equivalent to that of precipitated iron catalyst because during reactions $H_2$ is easily absorbed in its skeletal structure, and produces larger yields of lower-molecular-weight liquid fuel range hydrocarbons and smaller amounts of wax products. Also, in F-T synthesis processes it is easier to separate the skeletal iron catalyst from the reactor liquid medium and product, and thus achieves high recovery of the catalyst and thereby provides hydrocarbon liquid products essentially free of catalyst fines.

Although the skeletal iron catalyst of this invention is useful in either fixed bed or slurry bed type F-T reactors, its use in slurry bed reactors is preferred. For use in fixed bed catalytic reactors, the catalyst particle size should be 1.0–10 mm, and for use in slurry bed type reactors the catalyst particle size should be 0.1–5 mm. For Fischer-Tropsch synthesis process utilizing this skeleton iron catalyst, useful reaction conditions are 0.5–2.5:1 $H_2/CO$ molar ratio, 200–500° C. temperature, 0.5–5.0 mPa pressure.

DESCRIPTION OF INVENTION

The skeletal iron catalyst of this invention is made utilizing the following basic steps:

1. Catalyst Preparation. Mix iron powder and a non-ferrous metal powder selected from aluminum, antimony, silicon, tin or zinc in proportion of 20–80 wt. % iron and also add 0.01–5 wt % of promotor metal powder selected from calcium, copper, chromium, magnesium or potassium into a suitable furnace such as an electric induction furnace and mix together such as by magnetic stirring. Then melt the mixed powders under inert gas protection to form an iron alloy material, cool the iron alloy to room temperature and pulverize it to provide 0.1–10 mm particle size precursor material. Contact the iron alloy particles with 10–50% NaOH or KOH caustic solution in a stirred container under inert gas protection of argon, hydrogen or nitrogen; maintain reaction temperature 30–95° C. for 2–150 minutes to provide a desired substantial degree of extraction and/or leaching a major portion of the non-ferrous portion, and leaving particles containing mainly -Fe and some $Fe_3O_4$. Adding the iron alloy powder to the caustic solution is usually preferred rather than the reverse order, as it results in skeletal iron catalyst having larger pore size. The skeletal iron catalyst is further pulverized and screened to obtain a desired particle size range for synthesis reactions.

Alternatively the iron alloy precursor particles can be mixed with solid sodium hydroxide powder in a weight ratio to the iron alloy powder of 5–10:1, add deionized water to from a paste while stirring and allow the reaction to proceed for 5–30 minutes, then add fresh NaOH or KOH solution (10–50% concentration and maintain for 2–60 minutes at 30–95° C.

Another procedure for the catalyst preparation utilizes spraying the iron alloy precursor particles with a high concentration (40–60%) NaOH or KOH solution and maintaining the reaction in wet state for 5–30 minutes, then add additional NaOH or KOH 10–50% solution and maintain for 2–60 minutes at 30–95° C. temperature to effect the extraction and/or leaching step of removing most of the non-ferrous metal from the iron alloy particles. Then wash the iron particles with de-ionized water to pH=7, displace water with water-free ethanol, and store the resulting skeletal iron catalyst having 0.1–10 mm particle size in ethanol. Use of moderate extraction temperature of 50–60° C. appear to facilitate more pores and increased surface area, while longer extraction times cause undesirable partial oxidation of the iron particles. Following such extraction and/or leaching step, the catalyst can be further pulverized and screened as desired to obtain appropriate particle size for the F-T synthesis reactions. The catalyst is next treated by drying and reducing with hydrogen at high space velocity and at 200–500° C. temperature for 2–12 hours, then transferring the treated skeletal iron catalyst into water-free ethanol or liquid paraffin for storage before further usage.

2. Catalyst Utilization. Before the skeletal iron catalyst is evaluated or utilized in slurry-phase Fischer-Tropsch reaction, the catalyst is dried and reduced with hydrogen. Such drying is done by passing high space velocity hydrogen stream over the ethanol-containing catalyst, which is converted to mainly -Fe and is subsequently transferred into a liquid paraffin medium. Reaction conditions for slurry-phase Fischer-Tropsch synthesis process are 1.5–2.5:1 $H_2/CO$ molar ratio, catalyst loading 5–20 wt. % relative to the liquid paraffin, catalyst particle size 0.062–3.0 mm (62–3000), 200–500° C. temperature, 1.0–2.5 mPa pressure and reaction duration 40–240 hours. After completion of such catalytic reaction, the resulting catalyst/wax slurry material is removed, settled, and filtered. After slurry settling, the extent of a catalyst/wax separation is investigated. Also, the wax containing catalyst is extracted with xylene and analyzed for change in particle size distribution.

Compared with currently used fused iron and precipitated iron catalyst in Fischer-Tropsch synthesis processes, the skeletal iron catalyst of this invention provides the following advantages:

1. Catalyst preparation method is relatively simple and inexpensive.
2. For synthesis gas feed $H_2/CO$ molar ratio range of 0.5–2.5:1, the synthesis gas conversion is significantly higher than that obtained by using fused iron catalyst, and conversion of the feed is equivalent to that achieved by precipitated iron catalyst.
3. Product selectivity favors producing more lower molecular-weight hydrocarbons and less wax, resulting in lower slurry viscosity, which facilitates catalyst/wax separation.
4. Attrition resistance of the skeletal iron catalyst particles is improved, so that most of the skeletal iron catalyst can be recovered after synthesis reactions, resulting in very low catalyst loss and no significant effect on catalyst activity.

BRIEF DESCRIPTION OF DRAWINGS

The process of this invention for utilizing the skeleton iron catalyst will be described with reference to the following drawings, in which FIG. 1 depicts a flowsheet for a typical Fischer-Tropsch process synthesis utilizing a slurry phase reactor.

As shown by FIG. 1, separate feedstreams of pressurized CO at 10 and $H_2$ at 12 are provided having $H_2/CO$ molar ratio range of 0.5–2.5:1, together with skeletal iron catalyst having particle size range of 10–300 micron provided at 13. The feeds and catalyst are all introduced upwardly into a slurry type reactor 14 containing skeletal iron catalyst in a slurry bed 15. Reaction condition in reactor 14 are maintained at 200–350° C. temperature, 1.0–2.5 mPa pressure, and gas hourly space velocity of 0.5–3.0 L/g Fe/h.

From the reactor 14, a gas product is removed at 16. Also, a hydrocarbon liquid stream containing some catalyst particles is withdrawn from internal cup 17 as stream 18 and passed to a catalyst/liquid separator 20, which may be a settler vessel, hydroclone separator or filter. From the separator 20, a clean hydrocarbon liquid product containing minimal catalyst is removed at 22 and used catalyst particles concentrated in a small portion of the hydrocarbon liquid are withdrawn at 24. If desired, a portion of the used catalyst particles at 24 can be recycled at 25 back to the reactor 14, as needed to reduce catalyst loss and maintain the desired catalytic activity in the catalyst bed 15. The remaining portion of the used catalyst at 26 is discarded.

The skeletal iron catalyst preparation method and the catalyst use in Fischer-Tropsch synthesis process will be disclosed further by the following examples, which should not be construed as limiting in their scope.

EXAMPLE 1

Mix powders iron, aluminum and a small amount of copper promotor metal powder in a respective weight proportion of 33:66:1 in an electric induction furnace, heat and melt the metal powders to form an iron metal alloy, then cool it to room temperature and pulverize the resulting iron alloy to 0.1–1.0 mm size precursor particles. Then provide a desired amount of 25% NaOH caustic solution in a stirred container, add the iron alloy precursor particles under hydrogen flow into the caustic solution maintained at 85° C. temperature, and allow reaction to proceed for 30 minutes to extract and/or leach substantially the aluminum from the iron alloy particles. Wash the particles with deionized water to pH=7, displace water with water-free ethanol and store the resulting skeletal iron catalyst particles in ethanol.

Before being evaluated in a reaction system, the ethanol-containing skeleton iron catalyst is dried and reduced under high space velocity hydrogen at 300° C. for 2 hours, then transferred into reaction medium (liquid paraffin) in a stirred slurry autoclave reactor. Conditions for Fischer-Tropsch synthesis reaction are feed stream $H_2/CO$ molar ratio 2.0:1, catalyst loading 6 wt. %, particle size 0.100–0.125 mm, temperature 270° C., pressure 1.6 mPa, space velocity 1.0 hr$^{-1}$ and reaction time 40 hours. Test conditions and analytical results compared with precipitated iron catalyst are shown in Table 1 below.

EXAMPLE 2

Mix powders iron and aluminum together with a small amount of copper promoter metal powder in weigh proportion 33:66:1 into an electric induction furnace, heat and melt the powders to form iron metal alloy, then cool it to room temperature and pulverize the iron alloy to 0.1–1.0 mm size precursor particles as for Example 1. Then provide a desire amount of 25% concentration NaOH in a stirred container under hydrogen stream, add the Fe-Al alloy particles into the NaOH caustic solution maintained at 75° C. temperature, allow reaction for 30 minutes, to extract and/or leach substantially aluminum from the iron alloy particles. Then wash the particles with de-ionized water to pH=7, displace water with water-free ethanol and store skeletal iron catalyst particles in ethanol.

Next dry and reduce the ethanol-containing skeleton iron catalyst at 300° C. under high space velocity hydrogen for 2 hours, and then transfer the catalyst into liquid reaction medium (liquid paraffin) in a stirred slurry phase reactor. Conditions for slurry phase Fischer-Tropsch synthesis reaction are: catalyst loading 6 wt. %, particle size 0.100–0.125 mm, and reaction time 40 hours. Test conditions temperature 270° C., and analytical results are shown in Table 1.

EXAMPLE 3

Mix iron and aluminum powders together with a small amount of copper promoter powder in weight ratio of 33:66:1, in an electric induction furnace, heat and melt the metal powders to form an iron-aluminum alloy, then cool to room temperature and pulverize to 0.1–1.0 mm precursor particle size same as for Example 1. Then add desired amount of 25% concentration NaOH caustic solution to a stirred container, add the Fe-Al alloy particles to the caustic solution maintained at 65° C. temperature, and/or allow reaction for 30 minutes to extract and leach substantially the aluminum from the iron particles. Then wash the particles with de-ionized water to pH=7, displace water with water-free ethanol and store the resulting skeletal iron catalyst in ethanol.

Before the skeleton iron catalyst is evaluated in a reactor system, the ethanol-containing catalyst is dried and reduced at 300° C. under high space velocity $H_2$ for 2 hours, and is then transferred into slurry phase reaction medium (liquid paraffin) in a stirred reactor. Conditions for Fischer-Tropsch slurry phase reaction are: catalyst loading 6 wt. %, particle size 0.100–0.125 mm, temperature 270° C. reaction time 40 hours. The test conditions and analytical results are shown in Table 1.

EXAMPLE 4

Mix iron and aluminum metal powders and small amount of copper promoter powder in weight proportion of 33:66:1 in an electric induction furnace, heat and melt the metal powder to form an iron metal alloy, then cool it to room temperature and pulverize the metal alloy to 0.1–1.0 mm precursor particles size same as for Example 1. Then provide a desired volume of NaOH caustic solution 25% concentration into a stirred container, add the Fe-Al alloy particles into the caustic solution maintained at 95° C. temperature, and/or allow reaction for 30 minutes to extract and leach substantially all the aluminum from the iron particles. Then wash the particles with de-ionized water until pH=7, displace water with water-free ethanol, and store the skeletal iron catalyst in ethanol.

Before the skeleton iron catalyst is evaluated in a reactor system, the ethanol-containing catalyst is dried and reduced with high space velocity hydrogen at 300° C. for 2 hours; catalyst is subsequently transferred into a reaction medium (liquid paraffin) in a stirred autoclave reactor. Conditions for Fischer-Tropsch synthesis reaction are catalyst loading 6 wt %, particle size 0.100–0.125 mm temperature 270° C., and reaction time 40 hours. Test conditions and analytical results after reaction evaluation are listed below in Table 1.

TABLE 1

Comparisons of Skeletal Iron Catalyst and Precipitated Iron Catalyst in Fischer-Tropsch Slurry-Phase Synthesis Reaction under Identical Conditions*

| Example No. | Skeletal Iron Catalyst | | | | Precipitated Iron Catalyst |
|---|---|---|---|---|---|
| | 1 | 2 | 3 | 4 | |
| Cuastic Leaching Temperature for Iron Alloy Particles, °C. | 85 | 75 | 65 | 95 | — |
| Relative Separation of Catalyst in Slurry, %** | 20 | 20 | 25 | 25 | 100 |
| Catalyst Particle Size After Reaction, um | ~50 | 40–50 | 30–40 | ~50 | 1–10 |
| Conversion Decline in 50 hours, % | <5% | <5% | <5% | <5% | >20% |
| Catalyst Loss in 50 hours, % | 0.01 | 0.01 | 0.01 | 0.01 | 1.38 |

*Slurry-phase Fischer-Tropsch synthesis conditions: $H_2/CO$ = 2.0 (molar), space velocity = 1.0 hr$^{-1}$, temperature = 270° C., pressure = 1.6 MPa.

TABLE 1-continued

Comparisons of Skeletal Iron Catalyst and Precipitated Iron Catalyst in
Fischer-Tropsch Slurry-Phase Synthesis Reaction under Identical Conditions*

| Example No. | Skeletal Iron Catalyst | | | | Precipitated Iron Catalyst |
|---|---|---|---|---|---|
| | 1 | 2 | 3 | 4 | |

**After a slurry of catalyst and product liquid have settled for same length of time, relative separation of catalyst in product liquid is percentage of catalyst-containing wax relative to total volume of slurry; 100% implies no catalyst settling separation in the slurry.

Based on the above results, it is noted that the skeletal iron catalyst examples of this invention retain larger particle size, have improved attrition resistance during F-T reaction and are much more easily separated from the reaction product liquid than the known precipitated iron catalyst having smaller particles size after the reaction. Also, the decline in CO conversion and catalyst loss in product wax are substantially less for the skeletal iron catalyst, thereby indicating its lower catalyst consumption for the Fischer-Tropsch synthesis process.

EXAMPLE 5

Additional evaluations were made using this skeletal iron catalyst in a liquid paraffin medium in a slurry bed autoclave reactor. Reaction conditions for the $H_2$+CO feedstream for olefins production are: catalyst loading 5–20 wt % relative to the liquid paraffin, reaction duration 40–240 minutes. For a specific series of catalyst evaluation tests, the following results were obtained as listed below in Table 2.

TABLE 2

Reaction Results with Skeletal Iron Catalyst For $H_2$CO Feed

| Catalyst Parameters | |
|---|---|
| Particles size, mm | 0.062–0.30 |
| Surface area, m$^2$/g | 22.5 |
| Average pore size, nm | 12.5 |
| Reaction Conditions: | |
| System pressure, mPa | 1.1–1.5 |
| Reaction temperature, °C. | 273–283° C. |
| Gas hourly space velocity, L/g Fe/h | 1.0–2.0 |
| Conversion (single-pass), % | |
| CO | 82.7–94.5 |
| $H_2$ | 30.0–39.6 |
| Yields (single-pass), g/Nm$^3$ ($H_2$ + CO) | |
| $C_1$+ | 65.7–132.0 |
| $C_1$–$C_4$ | 43.8–78.3 |
| Hydrocarbon Distribution, % | |
| $C_1$ | 15.3–20.3 |
| $C_2$–$C_4$ | 39.0–49.3 |
| $C_2^=$–$C_4^=$/$C_2^0$–$C_4^0$ | 1.2–2.4 |

Based on these results, it is noted that for slurry-bed Fischer-Tropsch synthesis reaction at conditions of temperature range 180–330° C., pressure range 0.5–3.0 mPa, gas hourly space velocity in the range of 0.5–3.0 L/gFe/h, and feed gas $H_2$/CO mole ratio of 0.5–2.0:1, single-pass CO conversion of 83–95%, single-pass syngas conversion of 48–57%, single-pass hydrocarbon yield of 32–62 wt. % were achieved. About ⅕ to ⅓ of the hydrocarbon products are $C_2$–$C_4$ olefins.

Although this invention has been disclosed broadly and also identifies specific embodiments, it will be understood that modifications and variations can be made within the scope of the invention as defined by the following claims.

We claim:

1. A method for preparing a skeletal iron catalyst useful for Fischer-Tropsch synthesis processes, comprising the steps of:

a) providing a catalyst precursor metal alloy by mixing iron powder together with non-ferrous metal powder selected from aluminum, antimony, silicon, tin and zinc sufficient to provide iron content of 20–80 wt. % and 0.01–5.0 wt. % non-ferrous promotor metal powder selected from calcium, chromium, copper, magnesium and potassium; heating said mixed metal powders together under inert gas protection, while stirring said metal powders uniformly and melting the metal powders to form precursor iron alloy material, then cooling the melted iron alloy to room temperature and pulverizing the resulting iron alloy to provide skeletal iron catalyst precursor particles having 0.1–10 mm particle size;

b) contacting said skeletal iron alloy catalyst precursor particles with NaOH or KOH caustic solution having 10–50% concentration under inert argon, helium or hydrogen atmosphere, and heating the mixture to 30–95° C. temperature while maintaining reaction condition for 2–150 minutes and extracting and/or leaching out a major portion of the non-ferrous metal from the iron alloy precursor particles so as to provide a skeletal iron structure, then washing said particles with ion-free water until pH=7, displacing the water with alcohol, and placing the resulting skeletal iron catalyst particles in ethanol; and c) treating said skeletal iron catalyst particles by drying and reducing with hydrogen at high space velocity at 100–500° C. temperature for 2–12 hours, then transferring the treated skeletal iron catalyst into water-free ethanol or liquid paraffin for storage.

2. The skeletal iron catalyst preparation method of claim 1, wherein step (b) is treating said skeletal iron catalyst precursor particles by adding sufficient said NaOH or KOH caustic solution into a stirred container under hydrogen atmosphere and heating the solution to 30–95° C. temperature, then adding the iron alloy precursor particles into the caustic solution at suitable periodic time intervals, while maintaining the reaction condition for 5–150 minutes for extracting and /or leaching out a major portion of the non-ferrous metal from the iron alloy precursor particles, then washing the iron alloy precursor particles with deionized water until pH=7, displacing the water with alcohol, and placing the resulting skeletal iron alloy catalyst particles in ethanol.

3. The skeletal iron catalyst preparation method of claim 1, wherein step (b) is mixing said iron alloy precursor particles with solid sodium hydroxide (NaOH) powder at weight ratio of the sodium hydroxide to the iron alloy particles of 5–10:1, then adding deionized water dropwise to wet the mixture to provide a paste but not a fluid state while stirring so that reaction proceeds under a wet paste state; after the reaction has proceeded 5–30 minutes while gas release gradually decreases, adding to said paste mixture fresh NaOH or KOH 10–50% concentration solution and maintaining for 2–60 minutes at 50–95° C. temperature; then washing the iron alloy particles with deionized water to pH=7, displacing water with water-free ethanol and storing in ethanol.

4. The skeletal iron catalyst preparation method of claim 1, wherein step (b) includes placing said iron alloy precursor particles in a stirred container, spraying the particles with a 40–60% concentration NaOH or KOH solution, maintaining reaction in a wet but not fluid state for 5–30 minutes, adding NaOH or KOH caustic solution of 10–50% concentration and maintaining for 2–60 minutes at 50–90° C. temperature, then washing the iron alloy particles with deionized water to pH=7, then displacing the water with water-free ethanol and storing in ethanol.

5. The catalyst preparation method of claim 1, wherein said mixed metal powders are iron, aluminum and copper having an initial respective weight ratio of 33:66:1.

6. The catalyst preparation method of claim 1, wherein the step (b) catalyst precursor metal alloy extraction and/or leaching temperature is 50–95° C., and the treated skeletal iron catalyst particle size is 0.062–3.0 mm. (62–3000 microns).

7. The skeletal iron catalyst preparation method of claim 1, wherein said non-ferrous metal powder is aluminum and said promotor metal powder is copper.

8. The skeletal iron catalyst preparation method of claim 1, wherein said metal powder mixture is heated and melted in an electric induction furnace during magnetic stirring.

9. The skeletal iron catalyst preparation method of claim 1, wherein the iron alloy catalyst particle extracting/leaching temperature is 65–95° C., particle size is 30–50 microns, and relative separation of the catalyst in F-T synthesis product liquid slurry is 20–25% of the initial height in the product liquid slurry.

10. A method for preparing a skeletal iron catalyst useful for Fischer-Tropsch synthesis processes, comprising the steps of:
   a) providing a catalyst precursor metal alloy by mixing iron powder together with aluminum powder sufficient to provide iron content of 20–80 wt. % and 0.01–5.0 wt. % copper powder, heating said mixed metal powders together in an electric induction furnace under inert gas protection, while mixing said metal powders uniformly by magnetic stirring and melting the metal powders to form precursor iron alloy material, then cooling the melted precursor iron alloy to room temperature and pulverizing the resulting iron alloy to provide skeletal iron catalyst precursor particles having 0.1–10 mm particle size;
   b) contacting said skeletal iron alloy catalyst precursor particles with NaOH or KOH caustic solution having 10–50% concentration under inert hydrogen atmosphere by adding sufficient NaOH or KOH caustic solution having 10–50% concentration into a stirred container under the hydrogen atmosphere and heating the solution to 30–95° C. temperature, then adding the iron alloy precursor particles into the caustic solution at suitable periodic time intervals, while maintaining the reaction condition for 2–150 minutes and extracting and/or leaching out a major portion of the non-ferrous metal from the iron alloy precursor particles so as to provide a skeletal iron structure having particle size smaller than 10 mm, then washing said skeletal iron particles with ion-free water until pH=7, displacing the water with alcohol, and placing the resulting skeletal iron catalyst particles in ethanol; and
   c) treating the skeletal iron catalyst particles by drying and reducing with hydrogen at high space velocity at 200–500° C. temperature for 2–12 hours, then transferring the treated skeletal iron catalyst into water-free ethanol or liquid paraffin for storage.

11. A catalytic Fisher-Tropsch synthesis process utilizing skeletal iron catalyst in a reactor for producing hydrocarbon products, the process comprising:
   a) feeding CO and $H_2$ gas having $H_2$/CO molar ratio of 0.5–2.5:1 into a reactor containing a skeletal iron catalyst prepared according to claim 3;
   b) maintaining said reactor at conditions of 180–350° C. temperature, 0.5–5.0 mPa pressure, and gas hourly space velocity of 0.5–3.0 L/gFe/hr;
   c) withdrawing from the reactor a gas product and a hydrocarbon liquid product containing fine skeletal iron catalyst particles; and
   d) separating the fine skeletal iron catalyst particles from the hydrocarbon liquid product.

12. The catalytic synthesis process of claim 11, wherein the $H_2$/CO molar ratio is 2.0:1, reaction temperature is 270° C., pressure is 1.6 mPa and gas hourly space velocity is 1.0 L/gFe/h.

13. The catalytic synthesis process of claim 11, wherein the reactor is a fixed bed type reactor and the catalyst particle size is 1.0–10 mm.

14. The catalytic synthesis process of claim 11, wherein the skeletal iron catalyst is mixed with liquid paraffin and utilized in a slurry phase reactor, and the catalyst particles size is 0.1–3.0 mm.

15. The catalytic synthesis process of claim 14, wherein a portion of the skeletal iron catalyst particles separated from the hydrocarbon liquid product is recycled to the slurry phase reactor.

16. A catalytic Fisher-Tropsch synthesis process utilizing skeletal iron catalyst in a reactor for producing hydrocarbon liquid products, the process comprising:
   a) feeding CO and $H_2$ gas having $H_2$/CO molar ratio of 0.5–2.5:1 into a slurry phase reactor containing a fluid bed of skeletal iron catalyst prepared according to claim 3, said catalyst having 1.0–5.0 mm particle size;
   b) maintaining said reactor at conditions of 180–350° C. temperature, 0.5–3.0 mPa pressure and gas hourly space velocity of 0.5–3.0 L/gFe/hr;
   c) withdrawing from the reactor a gas product and a hydrocarbon liquid product containing fine skeletal iron catalyst particles; and
   d) separating the skeletal iron catalyst particles from the hydrocarbon liquid product, and recycling a portion of the separated catalyst-particles back to the slurry phase reactor.

* * * * *